(12) United States Patent
Licari et al.

(10) Patent No.: US 7,220,560 B2
(45) Date of Patent: May 22, 2007

(54) SECONDARY METABOLITE CONGENER DISTRIBUTION MODULATION

(75) Inventors: Peter J. Licari, Fremont, CA (US); Bryan Julien, Oakland, CA (US); Scott Frykman, Hayward, CA (US); Hiroko Tsuruta, Emeryville, CA (US)

(73) Assignee: Kosan Biosciences Incorporated, Hayward, CA (US)

(*) Notice: Subject to any disclaimer, the term of this patent is extended or adjusted under 35 U.S.C. 154(b) by 449 days.

(21) Appl. No.: 10/376,612

(22) Filed: Feb. 25, 2003

(65) Prior Publication Data

US 2004/0014183 A1 Jan. 22, 2004

Related U.S. Application Data

(63) Continuation-in-part of application No. 09/724,878, filed on Nov. 20, 2000, now Pat. No. 7,129,071.

(60) Provisional application No. 60/359,821, filed on Feb. 25, 2002.

(51) Int. Cl.
*C12P 19/62* (2006.01)
*C12N 1/20* (2006.01)

(52) U.S. Cl. .............. 435/76; 435/118; 435/252.3; 435/252.1; 536/23.2

(58) Field of Classification Search .............. 435/76, 435/325, 252.3, 419, 118, 254.11, 252.1; 536/23.2

See application file for complete search history.

(56) References Cited

OTHER PUBLICATIONS

Hopf et al., "Ambruticin S production in air-lift and stirred tank bioreactors." *Appl. Microbiol. Biotech.* (1990) 34: 350-353.
Tang et al., "Cloning and Heterologous Expression of the Epothilone Gene Cluster." *Science* (2000) 287: 640-642.
Frykman et al., "Control of secondary metabolite congener distributions via modulation of the dissolved oxygen tension," *Biotechnol. Prog.* (2002) 18: 913-920.
Carreras et al., "Saccharopolyspora erythraea-catalyzed bioconversion of 6-deoxyerythronolide B analogs for production of novel erythromycins," *J. Biotechnol.* (2002) 92: 217-228.
Regentin et al., "Production of novel FK520 analogs in *Streptomyces hygroscopicus*: improving titer while minimizing impurities." *J. Industrial Microbiol. Biotech.* (2002) 28: 12-16.
Pfefferle et al. "Improved secondary metabolite production in the genus Streptosporangium by optimization of fermentation conditions." *J. Biotechnol.* (2000) 80: 135-142.
Schneider et al. "Controlled regioselectivity of fatty acid oxidation by whole cells producing cytochrome P450BM-3 monooxygenase under varied dissolved oxygen concentrations." *Biotechnol. Bioengineer.* 64: 333-341.

*Primary Examiner*—Chih-Min Kam
(74) *Attorney, Agent, or Firm*—Gary W. Ashley (57) ABSTRACT

The present invention provides a generalized oxygen-limited cultivation method for myxobacterial strains engineered to heterologously express polyketides synthase (PKS) gene clusters under various oxygen tension conditions, modulating the polyketide congener distribution.

12 Claims, 11 Drawing Sheets

Figure 1. Erythromycin tailoring pathway

Figure 2. Structures of various epothilones.

Figure 3. Epothilone tailoring pathway.

(a)

(b)

Figure 4. Cultivation of strain K111-32.25 (EpoK$^+$) under (a) excess or (b) depleted oxygenation.

Figure 5. HPLC chromatographs of resin extracts of K111-32.25 (EpoK⁺) cultivated under (a) and (c) excess or (b) depleted oxygenation; and (c) strain K-111-40.1.

Figure 6. Conversion of 10,11-didehydro-epothilone B into Epo506.

Figure 7. Congener distribution between 10,11-didehydro-epothilone D and Epo506.

(a)

(b)

Figure 8. Modulation of oxygen tension during cultivation of *Sorangium cellulosum* strain Soce K111-150.17 shifts epothilone product distribution: (a) cell growth under 50 % dissolved oxygen (DO); and (b) and (c) low oxygen tension.

Figure 9. Epothilone congener titer time course under (a) control, (b) and (c) low Oxygen tension regimens.

Figure 10. HPLC chromatograph of epothilone A and B peaks from 50% Dissolved Oxygen (DO) growth conditions at t=112hrs. Retention times for epothilone A: 4.50 min, B: 5.06 min., C:9.74 min., and D:12.17 min.

Figure 11. HPLC chromatograph of epothilones congener shift to epothilone C, and D peaks in 0% Dissolved Oxygen condition at 112 hrs. Retention times for epothilone A: 4.50 min, B: 5.06 min., C:9.74 min., and D:12.17 min.

SECONDARY METABOLITE CONGENER DISTRIBUTION MODULATION

CROSS REFERENCE TO RELATED APPLICATIONS

The present application claims priority to U.S. patent application Ser. No. 60/359,821, filed Feb. 25, 2002. The present application claims priority to and is a continuation-in-part of U.S. patent application Ser. No. 09/724,878, filed Nov. 20, 2000, now U.S. Pat. No. 7,129,071, and is related to U.S. patent application Ser. No. 09/443,501, filed Nov. 19, 1999, now U.S. Pat. No. 6,303,342 B1, each of which is herein incorporated by reference in its entirety.

FIELD OF THE INVENTION

The present invention provides recombinant methods and materials for producing polyketides by recombinant DNA technology, and methods of modulating polyketide congener distribution by modulating oxygen tension. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, megalomicin, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874,748; 5,063,155; 5,098,837; 5,149,639; 5,672,491; 5,712,146; and 5,962,290; and Fu et al., 1994, *Biochemistry* 33: 9321-9326; McDaniel et al., 1993, *Science* 262: 1546-1550; and Rohr, 1995, *Angew. Chem. Int. Ed. Engl.* 34(8): 881-888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes. A third type of PKS found primarily in fungal cells has features of both the Type I and Type II enzymes and is referred to as a "fungal" PKS enzymes.

Modular PKSs are responsible for producing a large number of 12-, 14-, and 16-membered macrolide antibiotics including erythromycin, megalomicin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. *The polyketide metabolites;* E. Horwood: New York, 1991, incorporated herein by reference).

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al., 1994, *Science,* 265: 509-512, McDaniel et al., 1993, *Science* 262: 1546-1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, *Saccharopolyspora erythraea,* allows more facile construction of recombinant PKSs, and reduces the complexity of PKS analysis by providing a "clean" host background. This system also expedited construction of the first combinatorial modular polyketide library in *Streptomyces* (see PCT publication Nos. WO 98/49315 and 00/024907, each of which is incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, *Curr. Opin. Microbiol.* 1: 319-329; Carreras and Santi, 1998, *Curr. Opin. Biotech.* 9: 403-411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

There has been a great deal of interest in expressing polyketides produced by Type I and Type II PKS enzymes in host cells that do not normally express such enzymes. For example, the production of the fungal polyketide 6-methylsalicylic acid (6-MSA) in heterologous *E. coli,* yeast, and plant cells has been reported. See Kealey et al., January 1998, Production of a polyketide natural product in non-polyketide-producing prokaryotic and eukaryotic host, *Proc. Natl. Acad. Sci. USA* 95:505-9, U.S. Pat. No. 6,033,883, and PCT Patent Publication Nos. 98/27203 and 99/02669, each of which is incorporated herein by reference. Heterologous production of 6-MSA required or was considerably increased by co-expression of a heterologous acyl carrier protein synthase (ACPS) and that, for *E. coli,* media supplements were helpful in increasing the level of the malonyl CoA substrate utilized in 6-MSA biosynthesis. See also, PCT Patent Publication No. 97/13845, incorporated herein by reference.

The biosynthesis of other polyketides requires substrates other than or in addition to malonyl CoA. Such substrates include, for example, propionyl CoA, 2-methylmalonyl CoA, 2-hydroxymalonyl CoA, and 2-ethylmalonyl CoA. Of the myriad host cells possible for utilization as polyketide producing hosts, many do not naturally produce such substrates. In addition, to the manipulation of starting substrates and extender molecules there are manipulations of tailoring enzymes in various hosts to achieve diverse polyketide products. Furthermore, the host plays a significant role in polyketide congener production.

Bacteria are classified as strict aerobes (oxygen is necessary for growth), facultative anaerobes (oxygen is not necessary, but results in faster growth), aero tolerant anaerobes (oxygen has no effect on growth), strict anaerobes (oxygen prevents growth), or as microaerophilic (low concentrations of oxygen are required for growth). Oxygen-dependent intracellular processes in aerobic bacteria are mediated by oxidase and oxygenase enzymes. Most myxobacteria and actinomycetes are examples of strict aerobes. Growth of aerobic bacteria under microaerobic (low oxygen) conditions is of interest, as the culture's growth behavior and production of primary and secondary metabolites is often different than that typically observed under a condition of excess oxygenation (Winkelheusen et al., 1996; Schneider et al. 1999; Jensen et al., 2001; Liefke et al., 1990; Kaiser et al., 1994; Dick et al., 1994). References cited by author and year of publication are given a full citation below and each is herein incorporated by reference in its entirety.

Many secondary metabolites produced by members of the *Actinomycetales* and *Myxococcales* exhibit potent and varied biological activities. Polyketides are a class of these natural products produced by large multifunctional enzymes called polyketide synthases (PKS), often followed by modification via a subsequent enzymatic pathway (Carreras et al., 2000). The actions of these tailoring pathway enzymes can include glycosylations, hydroxylations, methylations, epoxidations, or a number of other changes to the core structure of the molecule.

Intermediate compounds along these tailoring pathways often possess biological potencies different from the final compound. Examples of this are the antibacterial compounds erythromycins B, C, and D, which can be processed into the more potent erythromycin A congener via an enzymatic pathway which includes the oxygen-dependent EryK hydroxylase ( see FIG. 1). Erythromycin B and its 13-substituted analogs are useful as precursors for the semisynthetic production of prokinetic gastrointestinal agents called motilides. However, erythromycin B is a very poor substrate for the EryK enzyme, and is essentially a shunt end product of this pathway (Lambalot et al., 1995). The ultimate fate of an erythromycin D molecule is then dependent upon a competitive reaction between the EryG methylase and the oxygen dependent EryK hydroxylase. It has been shown previously that the dissolved oxygen concentration during *S. erythraea* bioconversions of 6-deoxyerythronolide B (6-dEB) analogs is critical in determining if the erythromycin A or B congener is the predominant end product of these cultivations (Carreras et al., 1990).

The epothilones (FIG. 2) have recently generated interest as potential chemotherapeutic successors to the potent anti-cancer compound paclitaxel (Bollag et al., 1995, Gerth et al., 1996). Both paclitaxel (Taxol®) and the epothilones stabilize microtubules via the same mechanism of action, but the epothilones are effective against paclitaxel-resistant tumors and are more water-soluble (Kowalski et al., 1997, Su et al., 1997). At least 39 different epothilone variants and related compounds have been identified in the fermentation broth of the wild type producing organism, *Sorangium cellulosum* (Hardt et al.,2001). Epothilone D is reported to possess the highest therapeutic index of the four major epothilone congeners A, B, C, or D (Chou et al., 1998, Chou et al., 2001), but is produced in very low quantity by *S. cellulosum* (Gerth et al., 2000). The acyl transferase 4 (AT4) domain of the epothilone PKS can incorporate either a malonyl-CoA or a methylmalonyl-CoA extender unit, with this selectivity influencing the final ratio between epothilones A and B, or between epothilones C and D (Gerth et al., 2000). The epothilone D congener is a direct precursor for epoxidation into epothilone B (FIG. 3), catalyzed by the EpoK monooxygenase (Julien et al., 2000, Gerth, et al., 2001).

Erythromycin B and epothilone D are presented as examples of intermediates of secondary metabolite tailoring pathways in which the intermediate is sometimes the desired product. Additionally, there are many other examples of natural products in which a monooxygenase enzyme reaction is necessary for processing of a pathway intermediate into the end product. Examples include the bioconversion of compactin into the cholesterol-lowering drug, pravastatin (Serizawa et al., 1991, Watanabe et al., 1995; the production of the plant hormone, gibberellin (Tudzynski et al., 1998); the production of a fungal mycotoxin, sterigmatocystin (Keller et al., 2000); and the production of doxorubicin, an anti-cancer agent (Lomovskaya et al., 1999, Walczak et al. 1999).

The activity of these oxygen-dependent enzymes can be eliminated by genetic means, but this engineering may prove difficult or impossible to accomplish for various reasons. Directed genetic inactivation of a monooxygenase enzyme requires knowledge of and access to its sequence, as well as the ability to manipulate the DNA of the host organism. The present invention provides an alternate method for producing these intermediates as the major products, without requiring any genetic manipulation of the tailoring enzymes.

Given the potential for making valuable and useful polyketides in large quantities in heterologous host cells, there is a need for host cells capable of making polyketides in the modified distribution of congeners. The present invention helps meet that need by providing recombinant host cells, expression vectors, and methods for making polyketides in diverse host cells.

The following references provide background information on the present invention and are herein incorporated by reference in their entirety.

Winkelhausen, E.; Pittman, P.; Kuzmanova, S.; Jeffries, T. Xylitol formation by *Candida boidinii* in oxygen limited chemostat culture. *Biotechnol. Lett.* 1996, 18, 753-758.

Schneider, S.; Wubbolts, M.; Oesterhelt, G.; Sanglard, D.; Witholt, B. Controlled regioselectivity of fatty acid oxidation by whole cells producing cytochrome $P450_{BM-3}$ monooxygenase under varied dissolved oxygen concentrations. *Biotechnol. Bioeng.* 1999, 64, 333-341.

Jensen, N.; Melchiorsen, C.; Jokumsen, K.; Villadsen, J. Metabolic behavior of *Lactococcus lactis* MG1363 in mcroaerobic continuous cultivation at a low dilution rate. *Appl. Environ. Microbiol.* 2001, 67, 2677-2682.

Liefke, E.; Kaiser, D.; Onken, U. Growth and product formation of actinomycetes cultivated at increased total pressure and oxygen partial pressure. *Appl. Environ. Microbiol.* 1990, 32, 674-679.

Kaiser, D.; Onken, U.; Sattler, I.; Zeeck, A. Influence of increased dissolved oxygen concentration on the formation of secondary metabolites by manumycin-producing *Streptomyces parvulus*. *Appl. Environ. Microbiol.* 1994, 41, 309-312.

Dick, O.; Onken, U.; Sattler, I.; Zeeck, A. Influence of increased dissolved oxygen concentration on productivity and selectivity in cultures of a colabomycin-producing strain of *Streptomyces griseoflavus*. *Appl. Environ. Microbiol.* 1994, 41, 373-377.

Carreras, C.; Ashley, G. W. Manipulation of Polyketide Biosynthesis for New Drug Discovery. In *New Approaches to Drug Development;* Jolles, P., Ed.; Birkhauser-Verlag, Switzerland, 2000; pp 89-108.

Lambalot, R. H.; Cane, D. E.; Aparicio, J. J.; Katz, L. Overproduction and characterization of the erythromycin C-12 hydroxylase, EryK. *Biochemistry* 1995, 34, 1858-1866.

Carreras, C.; Frykman, S.; Ou, S.; Cadapan, L.; Zavala, S.; Woo, E.; Leaf, T.; Carney, J.; Burlingame, M.; Patel, S.; Ashley, G.; Licari, P. J. *Saccharopolyspora erythraea*-catalyzed bioconversion of 6-deoxyerythronolide B analogs for production of novel erythromycins. *J. Biotechnol.* 2002, 92, 217-228.

Bollag, D. M.; McQueney, P. A.; Zhu, J.; Hensens, O.; Koupal, L.; Liesch, J.; Goetz, M.; Lazarides, E.; Woods, C. M. Epothilones, a new class of microtubule-stabilizing agents with a taxol-like mechanism of action. *Cancer Res.* 1995, 55, 2325-2333.

Gerth, K.; Bedorf, N.; Höfle, G.; Irschik, H.; Reichenbach, H. Epothilons A and B: Antifungal and cytotoxic compounds from *Sorangium cellulosum* (myxobacteria)—production, physico-chemical, and biological properties. *J. Antibiot.* 1996, 49, 560-563.

Kowalski, R. J.; Giannakakou, P.; Hamel, E. Activities of the microtubule-stabilizing agents epothilones A and B with purified tubulin and in cells resistant to paclitaxel. *J. Biol. Chem.* 1997, 272, 2534-41.

Su, D. S.; Meng, D.; Bertinato, P.; Balog, A.; Sorensen, E. J.; Danishefsky, S. J.; Zheng, Y. H.; Chou, T. C.; He, L.; Horwitz, S. B. Structure-activity relationships of the epothilones and the first in vivo comparison with paclitaxel. *Angew. Chem. Int. Ed. Engl.* 1997, 36, 2093-2096.

Hardt, I.; Steinmetz, H.; Gerth, K.; Sasse, F.; Reichenbach, H.; Höfle, G. New natural epothilones from *Sorangium cellulosum,* strains So ce90/B2 and So ce90/D13: Isolation, structure elucidation, and SAR studies. *J. Nat. Products.* 2001, 64, 847-856.

Chou, T. C.; Zhang, X. G.; Balog, A.; Su, D. S.; Meng, D.; Savin, K.; Bertino, J. R.; Danishefsky, S. J. Desoxyepothilone B: An efficacious microtubule-targeted antitumor agent with a promising in vivo profile relative to epothilone B. *Proc. Natl. Acad. Sci. USA* 1998, 95, 9642-9647.

Chou, T. C.; O'Connor, O. A.; Tong, W. P.; Guan, Y.; Zhang, Z.; Stachel, S. J.; Lee, C.; Danishefsky, S. J. The synthesis, discovery, and development of a highly promising class of microtubule stabilization agents: Curative effects of desoxyepothilones B and F against human tumor xenografts in nude mice. *Proc. Natl. Acad. Sci. USA* 2001, 98, 8113-8118.

Gerth, K.; Steinmetz, H.; Höfle, G.; Reichenbach, H. Studies on the biosynthesis of epothilones: the biosynthetic origin of the carbon skeleton. *J. Antibiot.* 2000, 53, 1373-1377.

Julien, B.; Shah, S.; Zierman, R.; Goldman, R.; Katz, L.; Khosla, C. Isolation and characterization of the epothilone biosynthetic gene cluster from *Sorangium cellulosum*. *Gene.* 2000, 249, 153-160.

Gerth, K.; Steinmetz, H.; Höfle, G.; Reichenbach, H. Studies on the biosynthesis of epothilones: The PKS and epothilone C/D monooxygenase. *J. Antibiot.* 2001, 54, 144-148.

Serizawa, N.; Matsuoka, T. A two component-type cytochrome P-450 monooxygenase system in a prokaryote that catalyzes hydroxylation of ML-236B to pravastatin, a tissue-selective inhibitor of 3-hydroy-3-methylglutaryl coenzyme A reductase. *Biochem. Biophys. Acta.* 1991, 1084, 35-40.

Watanabe, I.; Nara, F.; Serizawa, N. Cloning, characterization and expression of the gene encoding cytochrome P-450sca-2 from *Streptomyces carbophilus* involved in production of pravastatin, a specific HMG-CoA reductase inhibitor. *Gene.* 1995, 163, 81-85.

Tudzynski, B.; Holter, K. Gibberellin biosynthetic pathway in *Gibberella fujikuroi:* evidence of a gene cluster. *Fungal Genet. Biol.* 1998, 25, 157-170.

Keller, N.; Watanabe, C.; Kelkar, H.; Adams, T.; Townsend, C. Requirement of monooxygenase-mediated steps for sterigmatocystin biosynthesis by *Aspergillus nidulans*. *Appl. Environ. Microbiol.* 2000, 66, 359-362.

Lomovskaya, N.; Otten, S.; Doi-Katayama, Y.; Fonstein, L.; Liu, X.; Takatsu, T.; Inventi-Solari, A.; Filippini, S.; Torti, F.; Columbo, A.; Hutchinson, C. R. Doxorubicin overproduction in *Streptomyces peucetius:* cloning and characterization of the dnrU ketoreductase and dnrV genes and the doxA cytochrome P-450 hydroxylase gene. *J. Bacteriol.* 1999, 181, 305-318.

Walczak, R.; Dickens, M.; Priestley, N.; Strohl, W. Purification, properties, and characterization of recombinant *Streptomyces* sp. Strain C5 DoxA, a cytochrome P-450 catalyzing multiple steps in doxorubicin biosynthesis. *J. Bacteriol.* 1999, 181, 298-304.

Julien, B.; Shah, S. Heterologous expression of the epothilone biosynthetic genes in *Myxococcus xanthus*. *Antimicrob. Agents Chemo.* In press.

Pirt, S. J. Oxygen Demand and Supply. In *Principles of Microbe and Cell Cultivation.* John Wiley and Sons, New York, 1975; pg. 84.

Lau, J.; Frykman, S.; Regentin, R.; Ou, S.; Tsuruta, H.; Licari, P. Optimizing the heterologous production of epothilone D in *Myxococcus xanthus. Biotechnol. Bioeng.* 2002, 78, 280-288.

Arras, T.; Schirawski, J.; Unden, G. Availability of $O_2$ as a substrate in the cytoplasm of bacteria under aerobic and microaerobic conditions. *J. Bacteriol.* 1998, 180, 2133-2136.

Tang, L.; Shah, S.; Chung, L.; Carney, J.; Katz, L.; Khosla, C.; Julien, B. Cloning and heterologous expression of the epothilone gene cluster. *Science* 2000, 287, 640-642.

Frykman, S.; Tsuruta, H.; Lau, J.; Regentin, R; Ou, S; Reeves, C.; Carney, J.; Santi, D.; Licari, P. Modulation of epothilone analog production through media design. *J. Ind. Microbiol. Biotechnol.* 2002, 28, 17-20.

SUMMARY OF THE INVENTION

In one embodiment, the present invention provides a method of modulating the polyketide congener distribution in a heterologous host cell without genetic manipulation of the polyketide synthase (PKS) genes or tailoring enzymes.

In one embodiment, the present invention provides metabolically engineered heterologous host cells that can be manipulated to produce a certain distribution of polyketide congeners by controlling oxygen tension during cultivation of said host cells.

In one embodiment, the present invention provides recombinant polyketide producing host cells that when cultivated under modulated oxygen tension conditions shift production of congeners. In one embodiment, the recombinant host cells are *Sorangium cellulosum* host cells that produce epothilones A and B and shift production to epothilone C and D when cultivated under depleted oxygen conditions.

In one embodiment, the polyketide produced by the heterologous host cell is epothilone, and the epothilone congener distribution is modulated to produce epothilone D by modulating the oxygen tension during cultivation.

In one embodiment, the epothilone congener distribution modulated by oxygen tension results in a higher ratio of epothilone D congener to epothilone C congener under excess oxygen tension. In another embodiment, the ratio of epothilone C to epothilone D congeners increases under depleted oxygen conditions. In one embodiment, the epothilone congeners are produced by a heterologous *Myxococcus xanthus* strain K111-32.25. In one embodiment, epothilones A and B are produced under excess oxygen tension, and epothilones C and D are produced under depleted oxygen tension in strain K111-32.25.

In one embodiment, the present invention provides a method of altering the specificity of acyltransferase (AT) domains of epothilone by modulating oxygen tension of module 4 of epothilone polyketide synthase (PKS) cluster without genetic manipulation. In one embodiment, the AT specificity of strain K111-32.25 is shifted to methylmalonyl-CoA resulting in a shift towards congeners with methyl group at C-12 (epothilones B or D).

In one embodiment, the present invention provides novel polyketides produced by metabolically engineered heterologous host cells having an active EpoK monooxygenase.

In one embodiment the novel polyketide produced by modulating oxygen tension during cultivation of a heterologous host cell is epothilone 506.

DETAILED DESCRIPTION OF THE INVENTION

The present invention provides an alternate method for producing polyketide intermediates as the major products, without requiring any genetic manipulation of the tailoring enzymes. The present methods of the present invention utilize host cells that have been deposited with the American Type Culture Collection (ATCC), 10801 University Boulevard. Manassas, Va. 20110-2209, under the Budapest Treaty and assigned deposit designation numbers. *Myxococcus xanthus* strain K111-32.25 was deposited May 1, 2000 under deposit designation PTA-1700, and *Myxococcus xanthus* strain K111-40.1 was deposited Jan. 18, 2001 under deposit number PTA-2712. *Sorangium cellulosum* strain K111-50.17 was deposited Mar. 27, 2003, under deposit designation PTA-5093.

A fed batch cultivation process has been previously described for the production of epothilone D in heterologous *M. xanthus* system. During these fed-batch cultivations, the dissolved oxygen tension can be modulated or regulated from excess oxygen, about 50% dissolved oxygen saturation to depleted oxygen or 0% dissolved oxygen measured, to achieve shifting of congener production. During fed-batch cultivations, the dissolved oxygen tension is maintained at 50% of air saturation through automated control of the agitation rate. When the upper range of the agitation rate is limited at a value insufficient for maintenance of this dissolved oxygen tension, continued increase of the culture's metabolic demand by its increasing cell density can eventually deplete the cultivation broth of oxygen. The culture is then in a metabolic state in which the rate of oxygen dissolution into the culture broth is equivalent to its consumption rate by the cells. This metabolic state results in a reading of zero from the dissolved oxygen probe, indicating that no residual oxygen activity is detected in the culture broth. This culture state can then be exploited to minimize the activity of oxygen-dependent tailoring enzymes of the processing pathway, while still providing enough oxygen to maintain culture viability.

Figure 4:
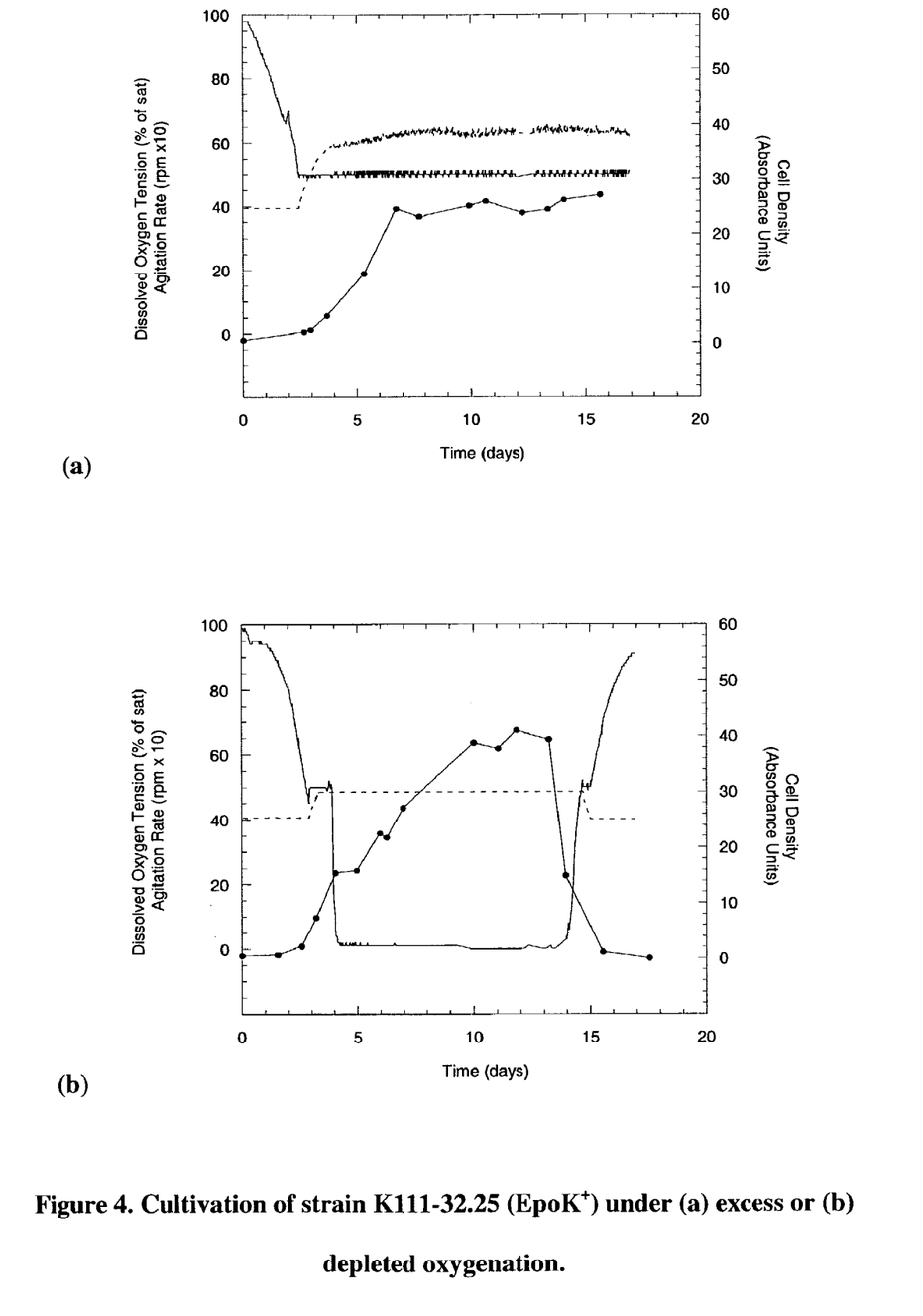
FIG. 4 shows cultivation of the strain K111-32.25 (EpoK$^+$) Panel (a) shows cultivation under excess oxygenation; Panel (b) shows cultivation with depleted oxygenation. Cultivation under deoleted oxygenation results in a 60% higher cell density than that obtained during cultivation of the same strain in the presence of excess oxygen.
Figure 5:
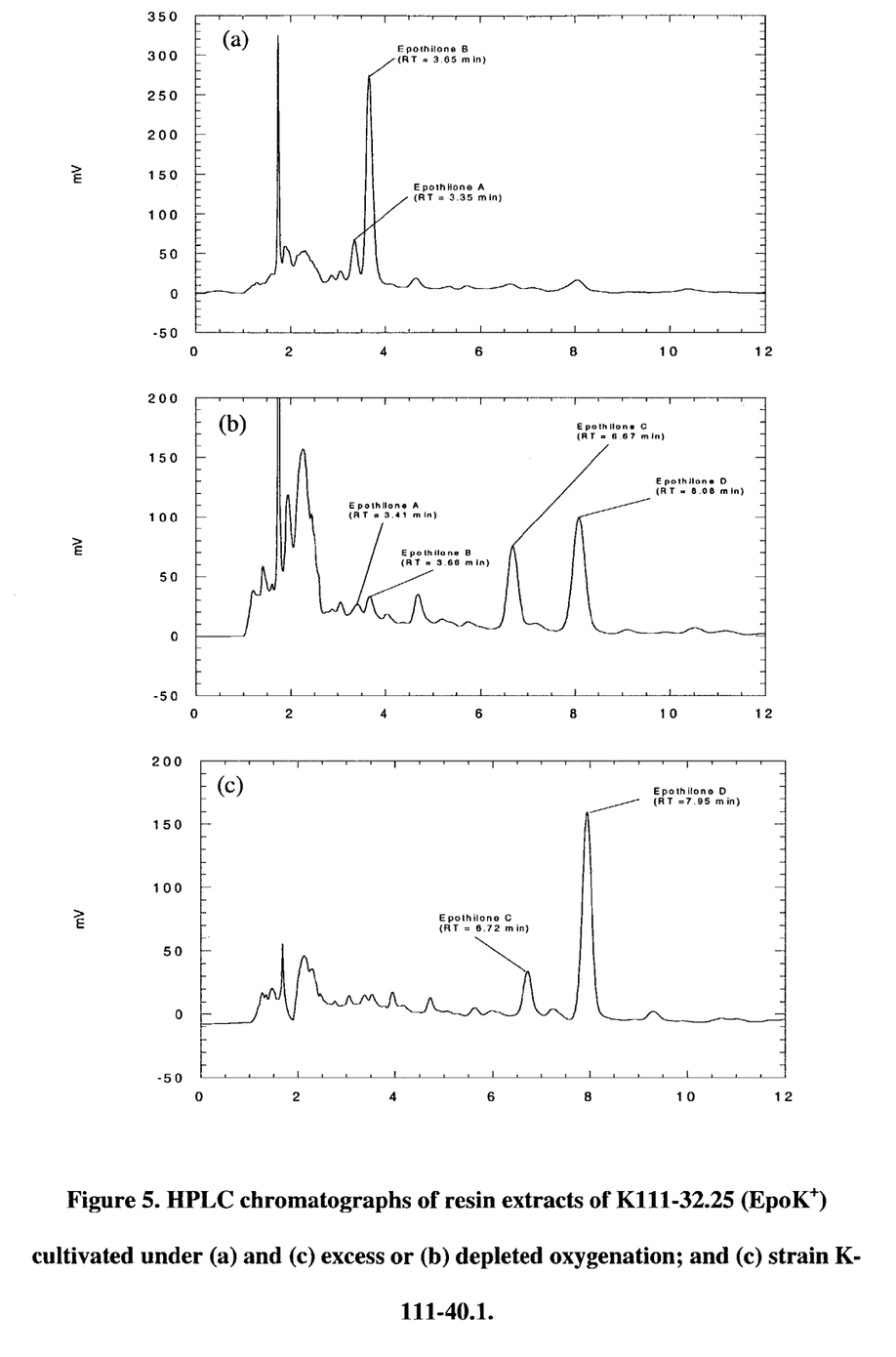
FIG. 5 shows HPLC chromatograms of resin extracts from fermentations of strain K111-32.25 (EpoK$^+$) or K111-40.1. Panel (a) shows the chromatogram resulting from cultivation of K111-32.25 under excess oxygen condition resulting in maximal activity of the EpoK enzyme, and production of apothilones A and B as the primary final products; Panel (b) shows the chromatooram resulting from cultivation of K111-32.25 under depleted oxygen conditions which limits the activity of this enzyme, resulting in pro-duction of epothilones C and D as the primary final products; Panel (c) shows the chromatogram resulting from cultivation of another strain (K111-40.1) under excess oxygenation in which the activity of the EpoK enzyme has been eliminated through genetic engineering.

Cultures of the K111-32.25 (ATCC deposit designation PTA-1700, May 1, 2000) epothilone B producing strain (EpoK+) were maintained at excess (50% of saturation) and depleted (0%) dissolved oxygen tensions during the entire epothilone production phase by controlling the agitation rate (FIGS. 4a,b). The excess oxygen condition results in maximal activity of the EpoK enzyme, and production of epothilones A and B as the primary final products (FIG. 5a). The depleted oxygen condition limits the activity of this enzyme, resulting in production of epothilones C and D as the primary final products (FIG. 5b). The result of these cultivations under depleted oxygenation is similar to those obtained with another strain (K111-40.1, ATCC deposit designation PTA-2712, Jan. 18, 2001) under excess oxygenation in which the activity of the EpoK enzyme has been eliminated through genetic engineering (FIG. 5c).

The modulation of the dissolved oxygen tension influences the ratio between the epothilone A and B (or C and D) congeners, in addition to the maximum total titer of the epothilones (See Example 2, Table 1). However, the time at which these maximum titers were attained was not dependent on the strain type or level of oxygenation in the bioreactor, as all three of the cultivation conditions described in Table 1 attained their maximum total epothilone titer around day 12. The acyl transferase 4 (AT4) domain of the epothilone PKS can incorporate either a malonyl-CoA or a methylmalonyl-CoA extender unit, with this selectivity influencing the final ratio between these epothilone congeners (17). The oxygen concentration may have an indirect influence on the intracellular pool distribution between malonyl- and methylmalonyl-CoA. Cultivation of strains K111-40.1 (EpoK$^-$) and K111-32.25 (EpoK$^+$) with excess oxygenation resulted in a pronounced shift towards the congener with the methyl group at C-12 (epothilones B or D), indicating that the cells favor production and/or incorporation of methylmalonyl-CoA under this condition (Table 1).

Cultivation of the EpoK$^+$ strain with depleted oxygenation resulted in a cell density that was 60% higher than that obtained during cultivation of the same strain in the presence of excess oxygen (FIGS. 4a,b). The exponential growth phase of the excess oxygen cultivation ceased on day 7, after which the cell density remained relatively constant (FIG. 4a). The specific growth rate ($\mu$) during this exponential phase was 0.7 d$^{-1}$. However, when the dissolved oxygen tension in the depleted oxygen cultivation reached zero on day 4 due to limitation of the agitation cascade response, this culture shifted from its exponential growth phase to a slower rate of growth ($\mu$=0.15 d$^{-1}$), which continued until day 12 (FIG. 4b). A similar pattern in growth behavior and increase in the maximum cell density was also observed with the EpoK$^-$ strain with depleted oxygenation, as well as with other genetically engineered M. xanthus strains which produce novel epothilones.

The increase in the cell density in the depleted oxygen cultivations can be attributed to (i) the cells may utilize nutrients at a different rate or in a different selective pattern during the slow growth imposed by oxygen limitation, thereby postponing the exhaustion of critical nutrients, (ii) the cultures produce different types or levels of potentially growth-inhibitory metabolites during oxygen limitation than excreted under excess oxygenation, or (iii) limitation of oxygen enhances or represses the expression of genes and the activity of enzymes involved in bacterial growth and respiration processes.

Figure 1:
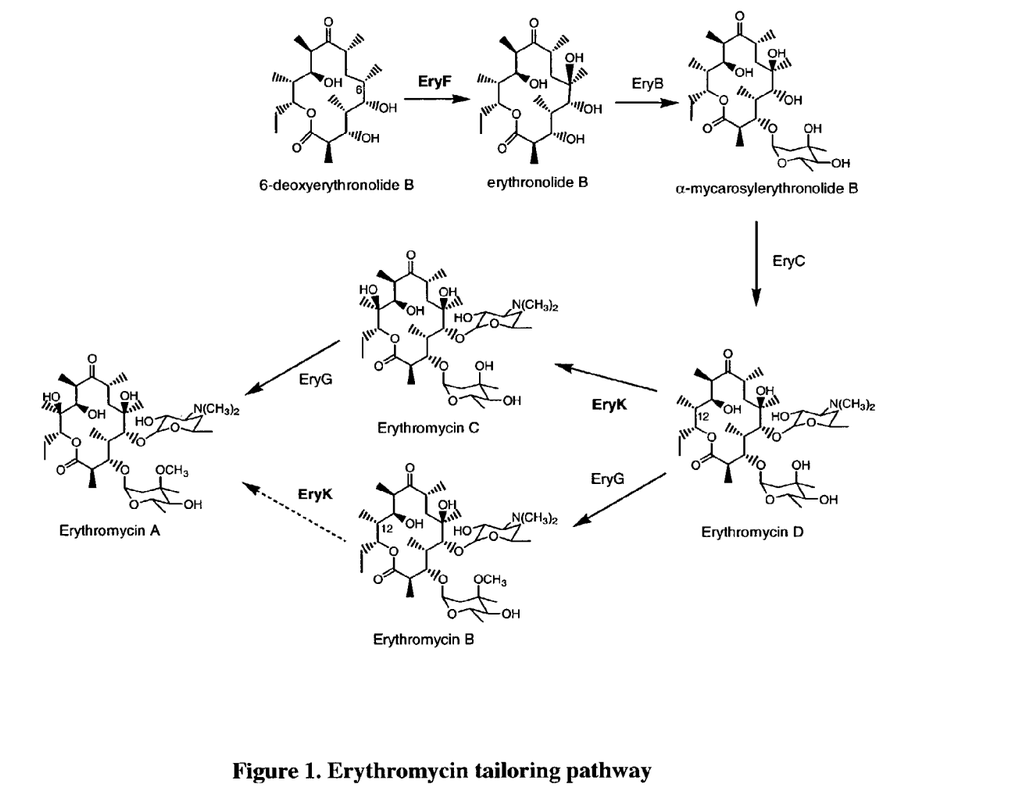
FIG. 1 shows erythromycins B, C, and D, which can be processed into the more potent erythromycin A congener via an enzymatic pathway which includes the oxygen-dependent EryK hydroxylase.

Control of the dissolved oxygen concentration during cultivation of bacterial cultures can have a dramatic effect on the cell density of the culture, as well as secondary metabolite titers and their congener distributions. This oxygen-limited cultivation strategy can be used to produce the intermediates of an oxygen-dependent tailoring pathway as the primary products. However, monooxygenase activity is not completely eliminated, but merely reduced to a fraction of the maximal rate typically seen under excess oxygen conditions. To prevent these intermediates from still being processed at a slower rate, it may be necessary for them to be stabilized in some manner. An example of this is the competitive reaction between the EryK hydroxylase and the EryG methylase for the erythromycin D substrate (FIG. 1). If the activity of EryK is reduced, EryG is able to catalyze conversion of erythromycin D into erythromycin B, a poor substrate for the EryK hydroxylase. This causes accumulation of the enzymatic pathway intermediate, erythromycin B. This pathway also contains another oxygen-dependent tailoring enzyme, EryF (FIG. 1), which remains capable of processing 6-deoxyerythronolide B (6-dEB) into erythronolide B under limited oxygen conditions.

Another example of this intermediate accumulation is the production of epothilone D during cultivation of a heterologous M. xanthus system with an active EpoK enzyme. The reduction in activity of an oxygen-depleted EpoK enzyme is apparently sufficient to slow the catalyzation of the epothilone D intermediate into its epothilone B congener and permit epothilone D to diffuse out of the cell and be bound and stabilized by the XAD-16 resin in the bioreactor. It has been shown that addition of epothilones C and D to shake flask cultures of a nonproducing strain of S. cellulosum which retains EpoK activity results in the diffusion of these compounds back into the cells and their transformation into epothilones A and B when no resin is present. Julien and coworkers have shown that this is also the case with a Myxococcus xanthus strain in which the epothilone PKS is nonfunctional, but EpoK is active (Julien et al. in press).

Novel epothilones are created by strains in which the epothilone polyketide synthase sequence has been manipulated (Julien et al., 2000, Tang et al., 2000). Modulation of the dissolved oxygen tension, in combination with the addition of specific precursors such as acetate and propionate to the production medium, permits the production of each of the four major epothilone congeners A, B, C, or D (FIG. 2) as the primary product from a single M. xanthus strain with an active EpoK enzyme (Frykman et al., 2002).

Increasing the serine concentration in the production medium increases its relative incorporation by the epothilone nonribosomal peptide synthetase (NRPS) into epothilone in place of cysteine (Frykman et al., 2002). Supplementation of serine to the production medium of strain K111-32.25, in conjunction with modulation of the dissolved oxygen concentration, results in the production of either of the oxazole epothilones $G_2$ or $H_2$ (FIG. 2) as the major product. Supplementation of serine, acetate, and/or propionate to the production medium, in addition to control of the dissolved oxygen tension permits the accumulation of any of the eight thiazole and oxazole major compounds (epothilones A, B, C, D, $G_1$, $G_2$, $H_1$, and $H_2$) as the primary product from a single M. xanthus strain. This approach should also permit the production and congener modulation of the oxazole counterparts of 10,11-didehydro-epothilone D and Epo506, as well.

The wild type epothilone PKS has been shown to produce nearly 35 additional epothilone variants in addition to epothilones A-D (Hardt et al., 2001). Similarly, it has been found that heterologous expression of the epothilone PKS and engineered variants results in a number of novel compounds in addition to the expected product. The concentration of these products can be enhanced or suppressed by the cultivation conditions. The ability to generate new compounds and modulate their distribution through manipulation of the cultivation conditions of a strain possessing a single genetic change in its PKS sequence demonstrates how powerful a tool PKS engineering, when combined with suitable physiological tuning, can be in the rapid generation of new natural products with potent biological activities.

A detailed description of the invention having been provided above, the following examples are given for the purpose of illustrating the invention and shall not be construed as being a limitation on the scope of the invention or claims.

EXAMPLE 1

Cultivation of Host Cells Under Modulated Oxygen Tension Conditions

Bacterial Strains. The epothilone polyketide synthase was cloned from *Sorangium cellulosum* SMP44, and introduced into *Myxococcus xanthus* strain DZ1 (Julien et al., in press). The *M. xanthus* epothilone B producer (K111-32.25) has a functional EpoK epoxidase (EpoK$^+$), while this enzyme has been genetically inactivated (EpoK$^-$) in the epothilone D producing strain (K111-40.1). The activity of the enoyl reductase (ER5) domain of the epothilone PKS was eliminated by introduction of a point mutation in both the K111-32.25 and K111-40.1 strains to produce strains K165-79.7 and K165-76.2, respectively. Strains K165-79.7 and K165-76.2 were engineered to produce 10,11-didehydro-epothilones B and D (FIG. 2), respectively.

Bioreactor Inoculum Expansion. All media components were obtained from Sigma (St. Louis, Mo.), unless otherwise specified. All *M. xanthus* cultures were initiated by reviving a 1 mL frozen cell bank vial in a sterile 25 mL glass tube containing 3 mL of CYE-MOM media (10 g/L of Casitone, a pancreatic digest of casein (Difco, Detroit, Mich.), 5 g/L yeast extract (Difco), 1 g/L MgSO$_4$.7H$_2$O (EM Science, Gibbstown, N.J.), and 2 mL/L of methyl oleate (Emerest 2301, Cognis Corporation, Cincinnati, Ohio)) for two days at 28° C. and 175 rpm. The entire contents of this tube were expanded for one day in 50 mL of CYE-MOM in a 250 mL baffled Erlenmeyer flask, and then this flask was used to inoculate 500 mL of CYE-MOM in a 2.8 L baffled Fernbach flask cultured for one day.

Fed-batch Bioreactor Cultivation. One hundred grams of XAD-16 hydrophobic resin (Rohm and Haas, Philadelphia, Pa.) and 10 g MgSO$_4$.7H$_2$O were combined in 4.5 L of deionized water, and sterilized (90 minutes, 121° C.) in a 5 L bioreactor (B. Braun, Allentown, Pa.). This resin is incorporated into the production medium to bind the epothilones and stabilize them from degradation. Two separate feed loops of a 250 g/L solution of the casein digest and methyl oleate were connected to the bioreactor, and a sufficient quantity of these two nutrients added to the bioreactor to bring the initial casein digest and methyl oleate concentrations to 5 g/L and 2 mL/L, respectively. Finally, 25 mL of a 0.22 μm filter-sterilized trace elements solution (1% (v/v) concentrated H$_2$SO$_4$, 14.6 g/L FeCl$_3$.6H$_2$O, 2.0 g/L ZnCl$_3$, 1.0 g/L MnCl$_2$.4H$_2$O, 0.43 g/L CuCl$_2$.2H$_2$O, 0.31 g/L H$_3$BO$_3$, 0.24 g/L CaCl$_2$.6H$_2$O, and 0.24 g/L Na$_2$MO$_4$.2H$_2$O) was added aseptically. The bioreactor was then inoculated (5% v/v) with the CYE-MOM seed culture, with the casein digest (2 g/L/day) and methyl oleate (3 mL/L/day) feeds initiated 48 hours following inoculation. Airflow was held constant in the bioreactor at 0.4 vvm (airflow volume per vessel volume per minute).

The dissolved oxygen tension in the bioreactor was monitored using an in situ polarographic oxygen sensor. This probe was calibrated at a 0% dissolved oxygen tension by equilibrating the production medium with 100% nitrogen, and at a 100% dissolved oxygen tension by equilibrating the production medium with air. The initial agitation rate was set at 400 rpm, with no additional bioreactor backpressure used during the cultivations. The saturation concentration of oxygen is approximately 7.7 mg/L at 28° C. (Pirt, S. J., 1975). The dissolved oxygen tension was maintained at a minimum of 50% of air saturation (3.9 mg/L O$_2$) by an agitation cascade in the excess oxygen cultivations, with the agitation rate limited to a maximum of 450 rpm in the depleted oxygen cultivations. The pH set point of 7.4 was maintained by automated addition of 2.5N H$_2$SO$_4$ and 2.5N KOH. The bioreactors were sampled daily for 12-14 days, followed by harvest of the resin.

Quantitation of Cell Density and Epothilone Titers. A 50 mL culture sample was removed daily from the bioreactor into a conical tube, and the broth decanted from the resin. A 1 mL aliquot of the broth was centrifuged in a 1.5 mL eppendorf tube at 12000 g for 5 minutes, and the supernatant removed by pipet. The cell pellet was resuspended with deionized water to a total volume of 1 mL, and the absorbance of this cell suspension measured spectrophotometrically at 600 nm (Genesys 20, Thermo Spectronic, Rochester, N.Y.). *Myxococcus xanthus* cultures grow as discrete unicellular rods, facilitating accurate optical density (OD) measurements. An OD measurement of 1.0 absorbance units correlates to a dry cell weight of approximately 0.3 g/L, with this correlation linear within the range of 0 to 40 OD units.

The XAD-16 resin was washed once with 45 mL of deionized water, again followed by its decanting. The resin was extracted in 25 mL of reagent-grade methanol for 30 minutes, and the epothilone titers quantitated by either HPLC or LC/MS. HPLC analysis was performed using a Hewlett Packard 1090 HPLC (Palo Alto, Calif.) with UV detection at 250 nm. A 50 uL aliquot of the methanol-extracted solution was injected across two 4.6×10 mm guard columns (MetaChem Inertsil C18 ODS 3, 5 μm, Ansys, Lake Forest, Calif.), and a longer column of the same material for chromatographic separation (4.6×150 mm). The method was isocratic with 70% acetonitrile and 30% water over a 12 minute run. LC/MS analysis was conducted on the same samples by injection into a PE Sciex API100LC (Perkin-Elmer, Shelton, Conn.), using an APCI source and the same guard and chromatographic columns as previously described. The chromatographic method was an acetonitrile/water gradient increased linearly from 35% to 100% over a ten-minute period.

EXAMPLE 2

Production of Novel Epothilones

Figure 2:
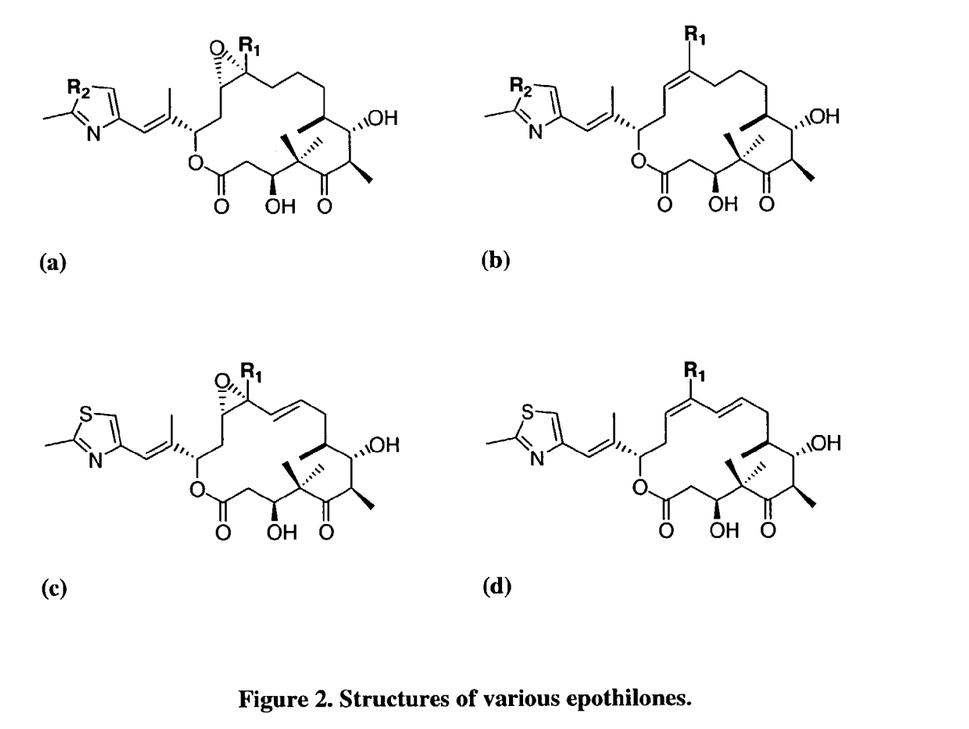
FIG. 2 shows the chemical structure of various epothilones. (a) Epothilone A ($R_1$=H; $R_2$=S); Epothilone B ($R_1$=$CH_3$; $R_2$=S); Epothilone $G_1$ ($R_1$=H; $R_2$=O); Epothilone $G_2$ ($R_1$=$CH_3$; $R_2$=O). (b) Epothilone C ($R_1$=H; $R_2$=S); Epothilone D ($R_1$=$CH_3$; $R_2$=S); Epothilone $H_1$ ($R_1$=H; $R_2$=O); Epothilone $H_2$ ($R_1$=$CH_3$; $R_2$=O). (c) 10,11-didehydro-epothilone A ($R_1$=H); 10,11-didehydro-epothilone B ($R_1$=$CH_3$). (d) 10,11-didehydro-epothilone C ($R_1$=H); 10,11-didehydro-epothilone D ($R_1$=$CH_3$).
Figure 3:
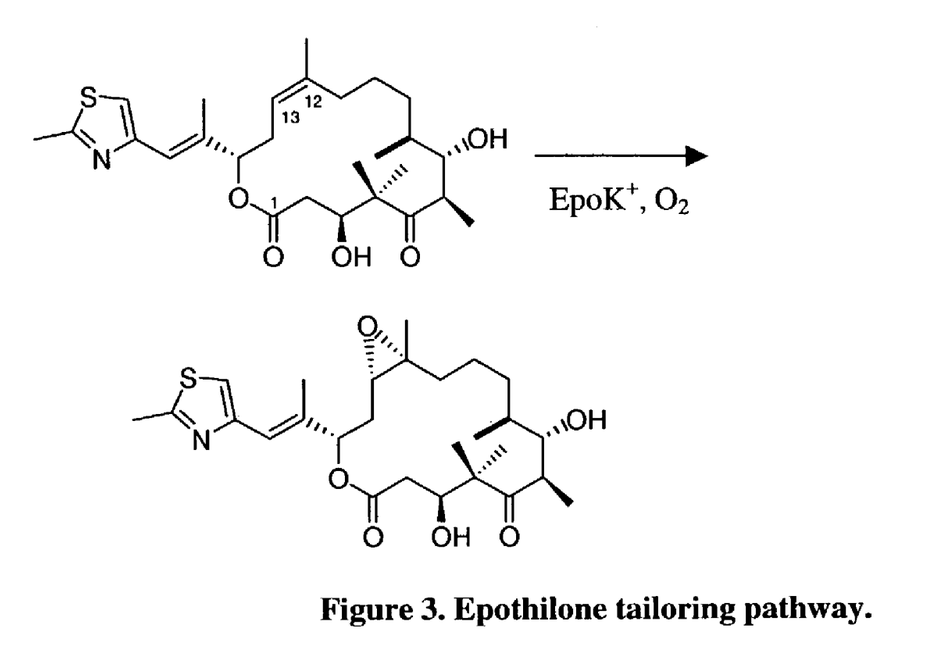
FIG. 3 shows epothilone D congener is a direct precursor for epoxidation into epothilone B catalyzed by the EpoK monooxygenase.
Figure 6:
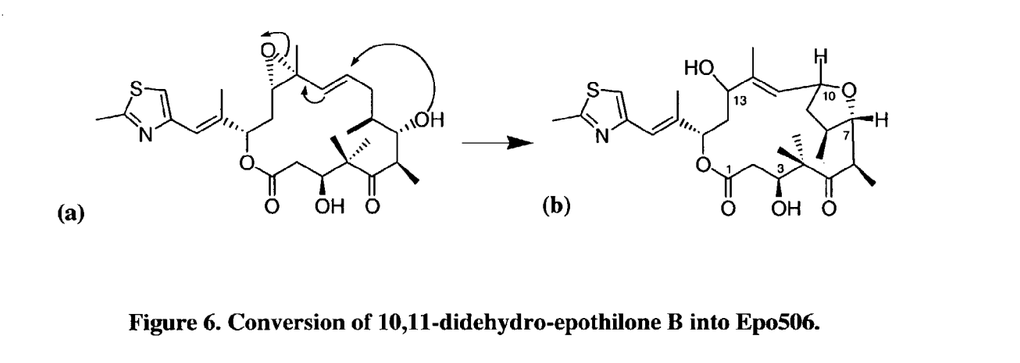
FIG. 6 shows vinylogous Payne rearrangement of (a) 10,11-didehydro-epothilone B converts to (b) Epo506 under excess oxygen conditions.

The epothilone PKS has been genetically altered to create strains of the present invention which produce novel epothilones which potentially may exhibit increased water solubility and/or potency against tumor cell lines. The oxygenation control method of the present invention was applied to an engineered *Myxococcus xanthus* production strain (strain K165-79.7, EpoK$^+$) which had been genetically engineered to produce a novel epothilone, 10,11-didehydro-epothilone B (FIG. 2). When its counterpart, strain K165-76.2 (EpoK$^-$), was cultivated under an excess oxygenation condition, 10,11-didehydro-epothilones C and D (FIG. 2) were found to be the sole products. The active EpoK enzyme in strain K165-79.7 was expected to catalyze epoxidation of this 10,11-didehydro-epothilone D intermediate into 10,11-didehydro-epothilone B (FIG. 6a) in the presence of excess oxygen. However, this compound was not detected; instead, a novel isomer (Epo506) was the primary product of these cultivations (FIG. 6b). High resolution mass spectrometry and one- and two- dimensional NMR were utilized to establish the structure of this tetrahydrofuran product (see Example 1).

Figure 7:
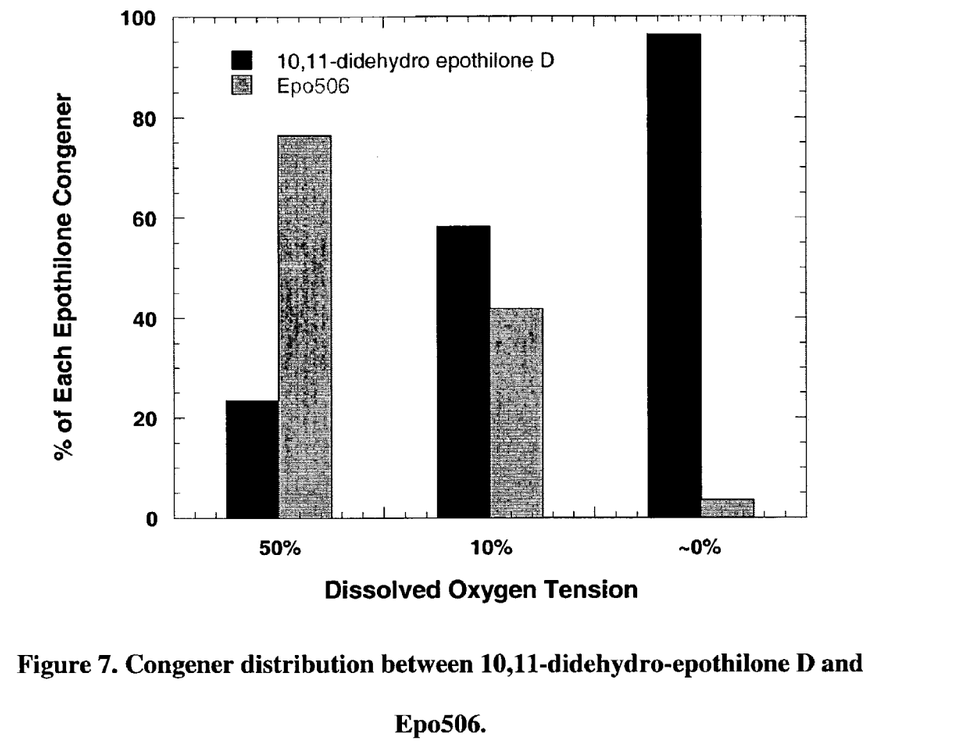
FIG. 7 shows cultivation of strain K165-79.7 under both depleted and excess oxygenation conditions resulting in shifting of the congener ratio between 10,11-didehydro-epothilone D and Epo506.

This observed result may be the product of a process whereby the 10,11-didehydro-epothilone B formed under these excess oxygen conditions, is then converted to Epo506 via a vinylogous Payne rearrangement, as summarized in FIG. 6. This reaction is favorable due to the epoxide opening to yield a relatively stable allylic carbocation intermediate. Cultivation of strain K165-79.7 under both depleted and excess oxygenation conditions resulted in shifting of the congener ratio between 10,11-didehydro-epothilone D and Epo506 (FIG. 7), which was similar to the congener shift between the epoxidated and non-epoxidated epothilone compounds obtained by cultivation of the parent strain, K111-32.25, under these two dissolved oxygen levels (Table 1).

A high-resolution mass spectrum of Epo506 was obtained with a Mariner TOF spectrometer (Applied Biosystems, Foster City, Calif.) configured with a turbo-ionspray source in positive ion mode. 1-D and 2-D NMR spectra of Epo506 were recorded at 300K with a DRX 400 spectrometer (Bruker, Billerica, Mass.) equipped with a QNP z-axis gradient probehead. Chemical shifts were referred to δ 7.26 and 77.0 for $^1$H and $^{13}$C spectra, respectively.

The molecular formula of Epo506 was determined to be $C_{27}H_{39}NO_6$ by HREIMS measurement of the [M+H]$^+$ peak at m/z 506.25887 (calculated for $C_{27}H_{40}NO_6S$ 506.25709), indicating the incorporation of one oxygen atom with respect to 10,11-didehydro-epothilone D. The $^{13}$C spectrum indicated that Epo506 possessed one double bond less than 10,11-didehydro-epothilone D, suggesting that Epo506 contains an additional ring. HSQC, HMBC, COSY, and TOCSY data allowed unambiguous assignment of the carbon connectivity. The chemical shifts at carbons 3, 7, 10 and 13 indicated that all four of these carbons were bonded to oxygen atoms. Two of these oxygenated carbons were postulated to be part of a cyclic ether to account for the molecular formula. The hydroxyl protons at carbons 3 and 13 were visible in both the 1-D and 2-D spectra, and their HMBC and COSY correlations to neighboring atoms confirmed their assignments. Therefore, the cyclic ether must include carbons 7 and 10, indicating a tetrahydrofuran structure. Significant Na$^+$ and K$^+$ adducts in the mass spectrum also confirmed that the ion observed at 506.3 by LC/MS is truly the molecular ion, and not a fragment generated upon ionization of a hypothetical parent diol.

TABLE 1

Epothilone Congener shifts in K111-40.1 strain.

| Cultivation Conditions (Strain, Oxygen Level) | Peak Epothilone B Titer (mg/L) | Peak Epothilone D Titer (mg/L) | Total (A–D) Epothilone Titer (mg/L) | Epothilone B:A Congener Ratio | Epothilone D:C Congener Ratio |
|---|---|---|---|---|---|
| K111-32.25 (EpoK$^+$) Excess Oxygen | 48 | 3 | 60 | 5.8:1 | 3.6:1 |
| K111-32.25 (EpoK$^+$) Depleted Oxygen | 3 | 19 | 34 | 2.5:1 | 1.7:1 |
| K111-40.1 (EpoK$^-$) Excess Oxygen | 0 | 30 | 36 | — | 5.2:1 |

EXAMPLE 3

Modulated Epothilone Congener Production in *Sorangium cellulosum* strain Soce90 K111-150.17

Modulation of dissolved oxygen during cultivation of heterologous host cells has been shown to shift polyketide congener distribution. In this example, an epothilone producing strain was subjected to oxygen tension resulting in shifting of epothilone congener distribution when cultivated under oxygen depletion conditions. *Sorengium cellulosum* strain Soce90 K111-150.17 (ATCC deposit designation PTA-5093 is a rifamycin-resistant mutant derived from Soce90 parent strain through UV mutagenesis (B. Julien, unpublished results). The cultivation methodologies and analytical methods used in this example were as done as described in Example 1 above.

Figure 8:
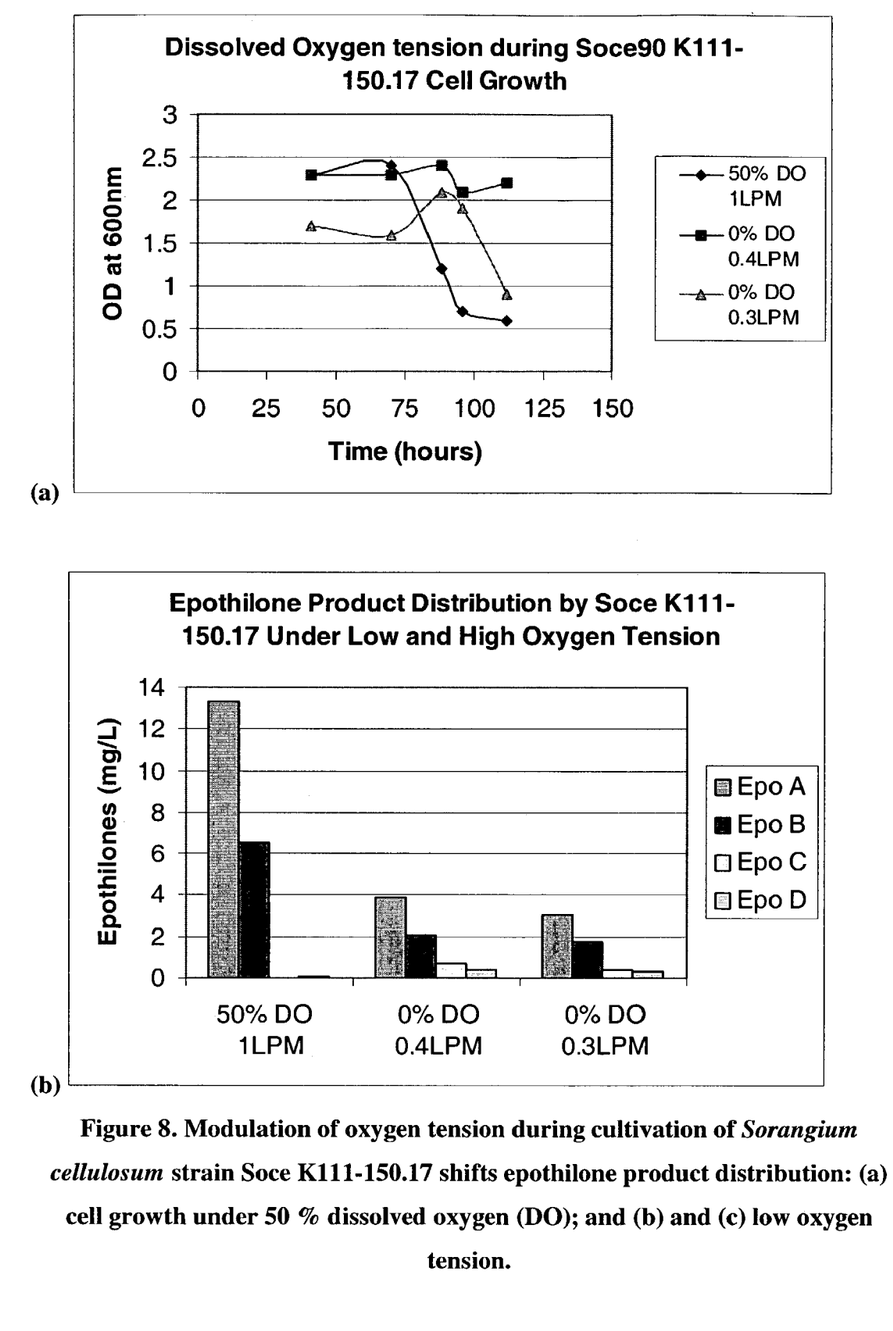
FIG. 8 shows modulation of oxygen tension during cultivation of *Sorangium cellulosum* strain Soce K111-150.17 shifts epothilone product distribution. Panel (a) shows cell growth under 50% dissolved oxygen (DO) with aeration at 1 liter per minute (LPM), at 0% DO with aeration at 0.4 LPM, and at 0% DO with aeration at 0.3 LPM. Panel (b) shows the distribution of epothilone products resulting from cell growth under the conditions shown in panel (a).

*Sorangium cellulosum* strain Soce90 K111-150.17 is an epothilone A and B producer that has an active epoK gene. FIG. 8 (a) illustrates the cell growth over time measured by optical density (OD) at 600 nm in three different dissolved oxygen (DO) conditions and airflow measured in 1 pm (liters per minute). FIG. 8(b) shows the effect of dissolved oxygen modulation on the epothilone product distribution. The *Sorangium cellulosum* strain Soce90 K111-150.17, an epothilone A and B producer, produces epothilones C and D at 0% depleted dissolved oxygen conditions. Table 2 shows the epothilone titers observed produced by the K111-150.17 strain under various oxygen tension conditions. The observed production of epothilone D is several fold higher under 0% depleted dissolved oxygen than at 50% excess dissolved oxygen for strain K111-150.17.

TABLE 2

Epothilone congener ratio shifts under depleted oxygen in strain K111-150.17.

| DO conc. | LPM | v/v/m | EpoA (mg/L) | EpoB (mg/L) | EpoC (mg/L) | EpoD/ mg/L |
|---|---|---|---|---|---|---|
| 50% | 1 | 0.2 | 13.3 | 6.54 | 0 | 0.08 |
| 0% | 0.4 | 0.2 | 3.87 | 2.06 | 0.66 | 0.35 |
| 0% | 0.3 | 0.15 | 3.04 | 1.71 | 0.4 | 0.32 |

Figure 9:
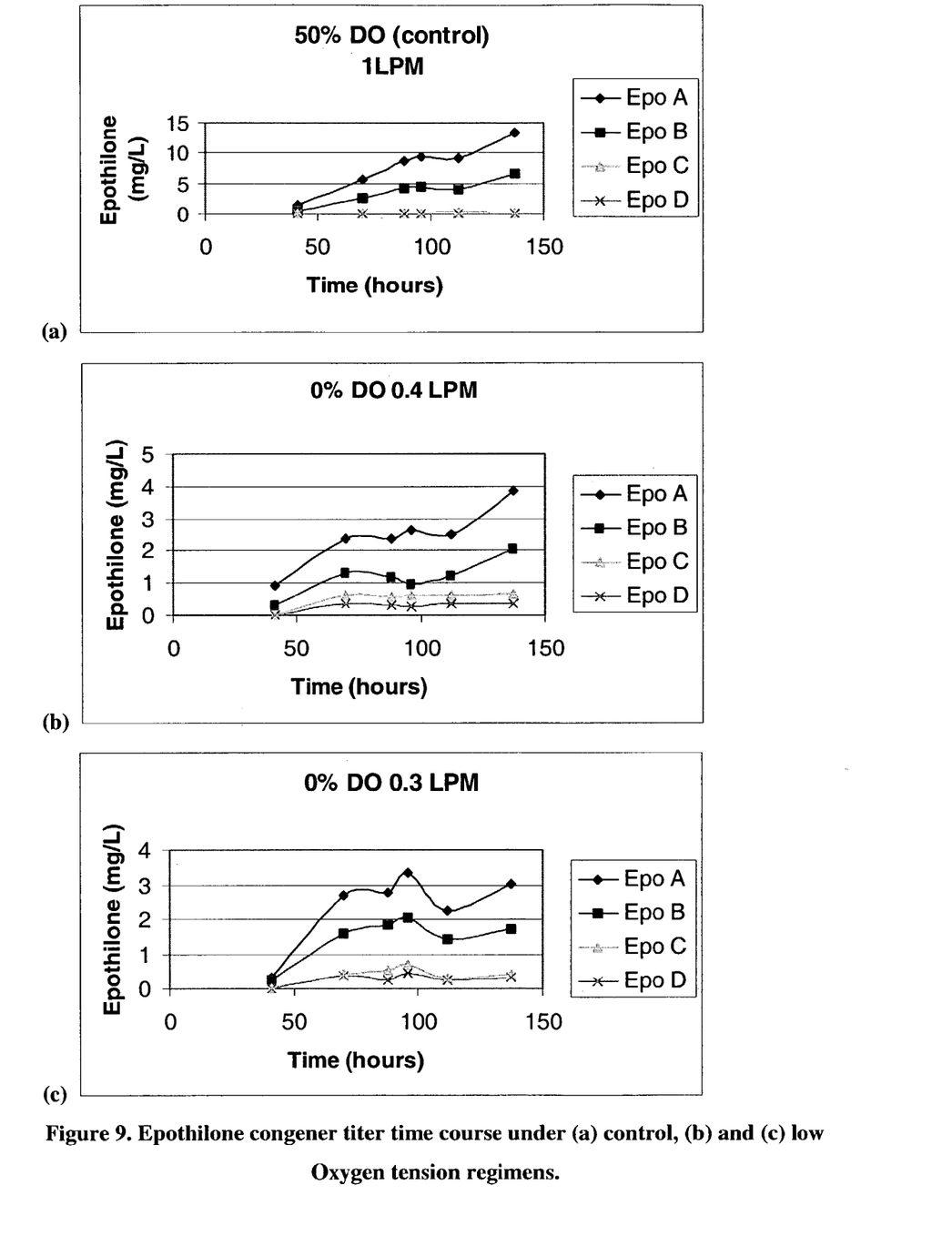
FIG. 9 shows titer time course for three different dissolved oxygen conditions. Panel (a) shows titers of epothilones A, B, C, and D under cultivation with 50% dissolved oxygen and an aeration of 1 LPM. Panel (b) shows titers of epothilones A, B, C, and D under cultivation with 0% dissolved oxygen and an aeration of 0.4 LPM. Panel (c) shows titers of epothilones A, B, C, and D under cultivation with 0% dissolved oxygen and an aeration of 0.3 LPM.
Figure 10:
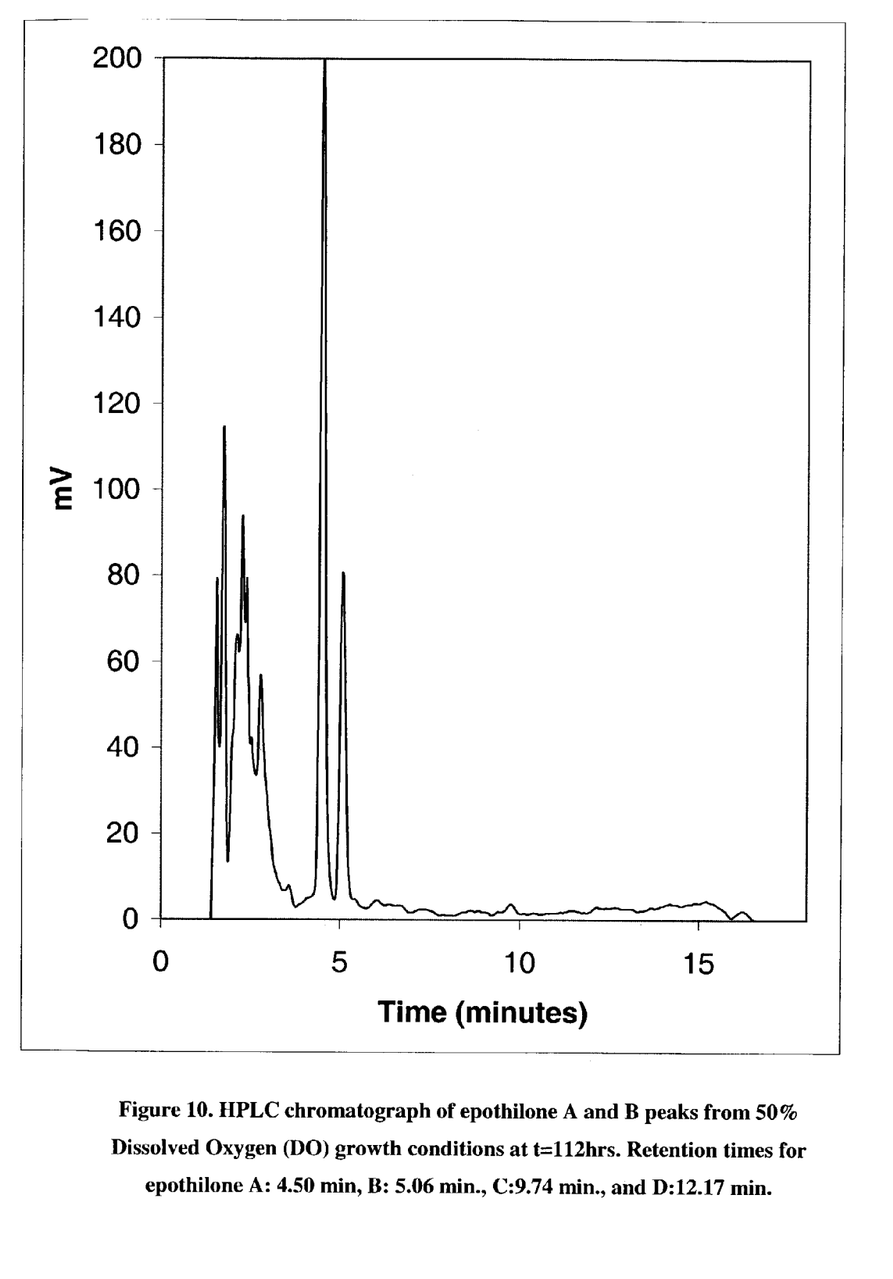
FIG. 10 shows an HPLC chromatogram showing epo A and epo B congener distribution from 50% dissolved oxygen condition at t=112 hrs.
Figure 11:
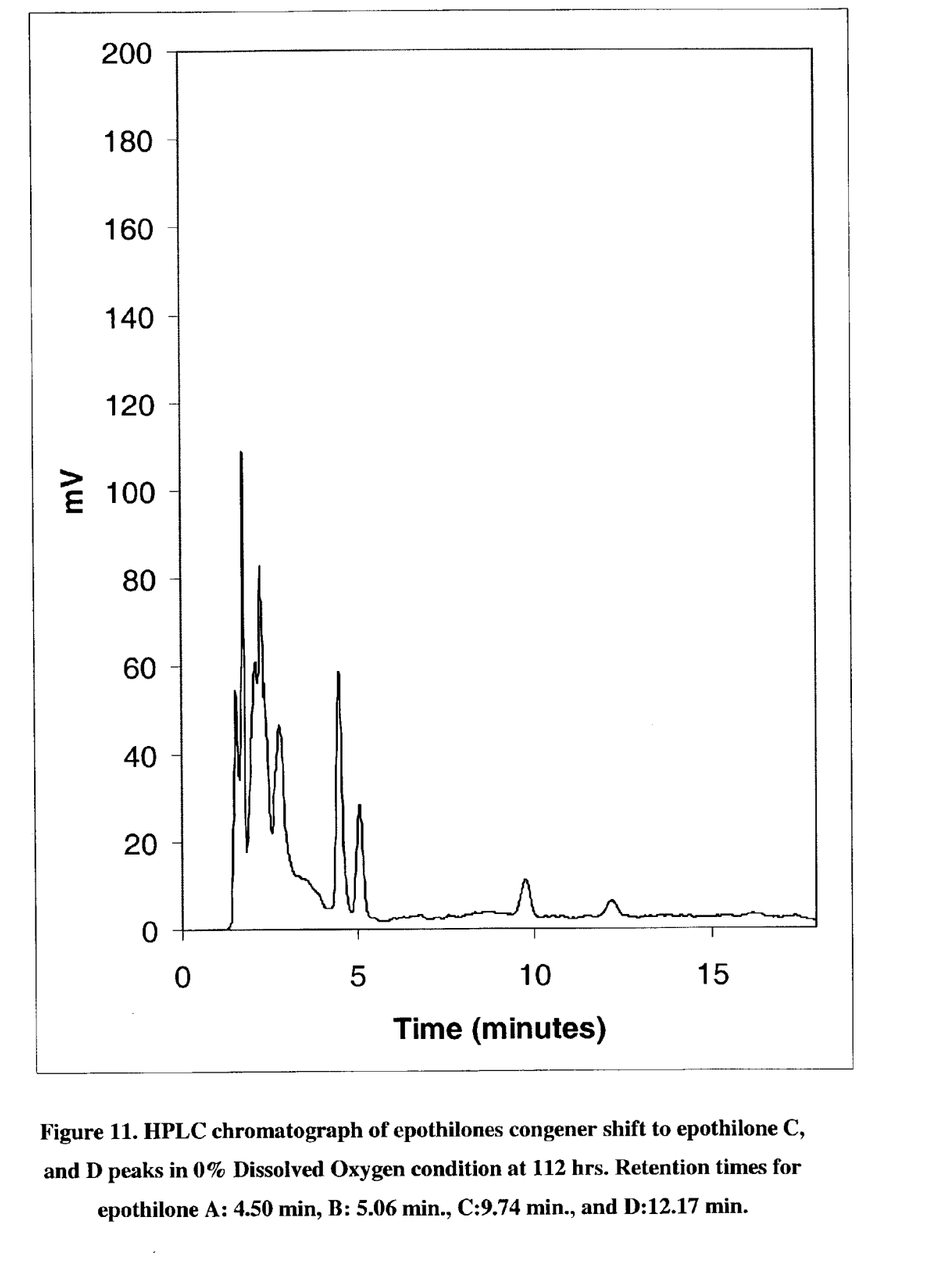
FIG. 11 shows an HPLC chromatogram of epothilones A, B, C, and D peaks from the 0% dissolved oxygen condition at 112 hrs.

FIG. 9 shows a time course of epothilone A, B, C and D production by strain K111-150.17 in three different dissolved oxygen regimens showing higher epothilone D production under low oxygen tension regimens. HPLC chromatograms from the fermentations conducted under 50% dissolved oxygen tension and 0% oxygen tension show the almost exclusive epothilone A and B production at 50% oxygen tension and the higher amounts of epothilone C and D produced under a low oxygen tension.

The foregoing examples are for illustration of the present invention and will be understood by those of skill in the art that they are non-limiting embodiments of the invention as claimed by the inventors in the following claims.

The invention claimed is:

1. A method of increasing the ratio of epothilone congeners having a C-12 methyl to epothilone congeners having a C-12 hydrogen produced by a *Myxococcus xanthus* host cell, comprising the steps of cultivating said host cell in growth medium under conditions that lead to the production of epothilone, and modulating oxygen tension to about 50% of saturation, resulting in increasing the ratio of epothilone congeners having a C-12 methyl.

2. The method of claim 1 wherein the epothilone congeners are epothilones C and D, and wherein the ratio of epothilone D to C congener production is at least 3 to 1 under oxygen tension conditions of about 50% saturation.

3. The method of claim 2 wherein the myxobacterial host cell is EpoK$^-$.

4. The method claim 2 wherein the myxobacterial host cell is *Myxococcus xanthus* strain K111-40.1.

5. A method of modulating epothilone congener distribution production ratio in a myxobacterial host cell, wherein said congeners differ in having either a 12,13-alkene or a 12,13-epoxide, comprising the steps of cultivating said host cell in growth medium under conditions that lead to the production of epothilones, and modulating oxygen tension during cultivation of said host cells, resulting in shifting production of species of said epothilone congeners.

6. The method of claim 5 further comprising the step of supplementing the growth medium with serine.

7. The method of claim 5 further comprising the step of supplementing the growth medium with acetate.

8. The method of claim 5 further comprising the step of supplementing the growth medium with propionate.

9. The method of claim 5 wherein said host cell is *Myxococcus xanthus* with an active EpoK$^+$ monooxygenase.

10. The method of claim 5 wherein said host cell is *Sorangium cellulosum* strain Soce90 K111-150.17.

11. The method of claim 5 wherein said host cell is *Myxococcus xanthus* strain K111.32.25.

12. The method of claim 5 wherein the ratio of epothilone congener production is shifted from epothilone A and B to epothilone C and D congener distribution under oxygen tension conditions of 0% of saturation.

* * * * *